(12) United States Patent
Patel-Framroze

(10) Patent No.: US 12,421,440 B2
(45) Date of Patent: Sep. 23, 2025

(54) PROTEIN HYDROLYSATE COMPOSITION THAT INCREASES COALBED METHANE PRODUCTION

(71) Applicant: Bomi Patel-Framroze, Portola Valley, CA (US)

(72) Inventor: Bomi Patel-Framroze, Portola Valley, CA (US)

( * ) Notice: Subject to any disclaimer, the term of this patent is extended or adjusted under 35 U.S.C. 154(b) by 134 days.

(21) Appl. No.: 17/559,675

(22) Filed: Dec. 22, 2021

(65) Prior Publication Data

US 2022/0112423 A1   Apr. 14, 2022

(51) Int. Cl.
*C09K 8/582* (2006.01)
*C12N 9/48* (2006.01)
*E21B 43/00* (2006.01)
*E21B 43/16* (2006.01)

(52) U.S. Cl.
CPC ............... *C09K 8/582* (2013.01); *C12N 9/48* (2013.01); *E21B 43/006* (2013.01); *E21B 43/16* (2013.01)

(58) Field of Classification Search
CPC ......... C09K 8/582; C12N 9/48; E21B 43/006; E21B 43/16
See application file for complete search history.

(56) References Cited

U.S. PATENT DOCUMENTS

| | | | |
|---|---|---|---|
| 2004/0203134 A1* | 10/2004 | Pyntikov | C12P 21/06 435/252.1 |
| 2005/0037109 A1* | 2/2005 | Soerensen | A23J 1/04 426/56 |
| 2010/0252255 A1* | 10/2010 | Budwill | C12P 5/023 166/246 |
| 2019/0037882 A1* | 2/2019 | Framroze | A23J 3/34 |
| 2021/0008174 A1* | 1/2021 | Destaing | A23K 20/147 |
| 2022/0279814 A1* | 9/2022 | Guerard | A61K 31/202 |

FOREIGN PATENT DOCUMENTS

WO   WO-2021019093 A1 *   2/2021   ................ A23J 1/04

* cited by examiner

*Primary Examiner* — Alicia Bland

(57) ABSTRACT

This invention provides a composition and a method for increasing biogenic methane gas production from subterranean coal deposits. The composition and method provides a nutrient protein hydrolysate that contains less than 0.5 percent of the amino acid L-tyrosine, which is most effective in significantly increasing methane gas released from subterranean coal deposits.

4 Claims, 4 Drawing Sheets

Figure 1:
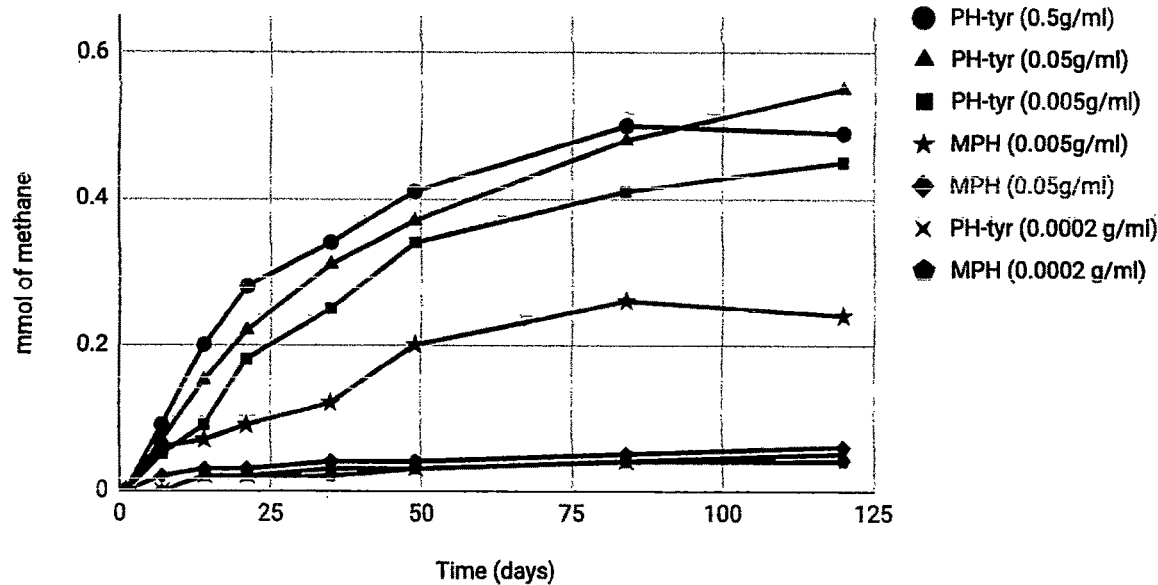

FIGURE 1 - Comparison of MPH and PH-tyr in methane production

PROTEIN HYDROLYSATE COMPOSITION THAT INCREASES COALBED METHANE PRODUCTION

FIELD

The present invention relates to a novel composition of a protein hydrolysate that contains less than 0.5 percent of free L-tyrosine amino acid by weight of total protein hydrolysate and a method of use of said protein hydrolysate for in situ increasing biogenic methane gas production from subterranean coal deposits.

BACKGROUND

Coalbed methane gas is an energy resource of global significance, with the emergence of active coalbed methane gas production in Canada, Australia, India and China (Palmer, I.; *Coalbed methane completion: A world view, Int. J of Coal Geology,* 2010, 82(3-4), p 184-195) and smaller start-up efforts in countries like Germany, England, France, Turkey, and Colombia. Coalbed methane gas is typically commercially exploited from shallow subterranean coal deposits with high gas permeable coalbeds. All coal mines also produce methane and during active coal mining operations the methane is actually an undesired byproduct that has to be safely removed using venting and burn-off systems. Once they have ceased commercial coal mining operations, mines are typically sealed and shut.

However, since they still often continue to produce methane gas, they need to also be set up with an active venting system that allows for controlled release of the built up methane gas into the atmosphere thus preventing explosions and collapse of the closed coal mines. If the methane concentration is adequately high, this methane off-gas is sometimes exploited to generate electricity via combustion.

Once the methane levels in the coal mines drop below a level suitable for combustion, these mines are finally abandoned and the methane that is still slowly produced is simply vented into the atmosphere, creating many significant local (smell and safety) and global (methane has 50× the global warming potential of carbon dioxide) environmental issues.

Coalbed methane gas in coal deposits can occur from both thermogenic and microbial (biogenic) processes. Thermogenic methane is geological methane and cannot be regenerated. Biogenic methane is produced by methanogenic microorganisms and hence can be continuously produced in microbially populated coal deposits.

If a commercially viable method could be found to increase the biogenic microbial methane present in some of these abandoned and sealed mines, the methane could be collected and continuously combusted to generate electricity. One mole of methane when combusted produces one mole of carbon dioxide. One mole of carbon dioxide has $\frac{1}{50}×$ the greenhouse effect of one mole of methane. Hence releasing one mole of carbon dioxide after electricity generation instead of venting one mole of waste methane, from an abandoned coal mine, directly into the atmosphere is a renewable, clean source of energy and is already of great interest to energy producers.

Generation of biogenic methane in coal deposits is controlled by three factors; a) the bioavailability of the coal carbon, b) the presence of a microbial consortium that can convert the carbon to methane, and c) a nitrogen rich nutritive environment that can support microbial growth and methanogenesis.

Biogenic methane gas from coal comes about from a cascade of biochemical reactions under substantially anaerobic conditions. A variety of microorganisms that form a symbiotic consortium degrades the coal in a sequential manner, such that the output compounds produced by upstream microorganisms serve as the nutritive compounds for downstream ones.

In one manifestation of increasing biogenic methane, proteins and peptides present in a hydrolyzed protein micronutrient mixture maybe be consumed by microorganisms such as in a fermentation broth to yield amino acids, carbon dioxide, acetates and hydrogen and the acetates may be cleaved further by the same microorganisms to produce more methane through a putative fermentation-only pathway.

In another potential cascade sequence, proteins and peptides present in the hydrolyzed protein micronutrient mixture may be initially consumed by fermentation microorganisms such as those described above to yield the amino acids, carbon dioxide, acetate and hydrogen. These are further used by the next downstream acetogenic microorganisms to produce more carbon dioxide and more acetate, which being the primary nutritive compounds for methanogenic microorganisms results in the production of significantly more biogenic methane from the coal deposits. Prior art has described the potential to exploit coalbed microorganisms to produce more biogenic coalbed methane gas in real time and enhance the methane output of coalbed methane gas wells. (Jones et al., *Stimulation of Methane Generation from Nonproductive Coal by Addition of Nutrients or a Microbial Consortium. Appl. Environ. Microbiol.* 2010, 76(21), p 7013; Ulrich and Bower; *Active methanogenesis and acetate utilization in Powder River Basin coals*, United States. *Int. J. Coal Geology.* 2008, 76(1-2), p 25-33; Scott, A. R., *Improving Coal Gas Recovery with Microbially Enhanced Coalbed Methane. Coalbed Methane: Scientific, Environmental and Economic Evaluation.* 1999, pp 89-110).

However, the rate of increased methanogenesis in coal deposits, appears to be slow in-situ and needs to be further accelerated for methane recovery to be economically viable (Fakoussa, R. M., Hofrichter; M, *Biotechnology and microbiology of coal degradation. Appl. Environ. Microbiol.* 1999, (52), p 25-40). Budwill et al (*Microbial diversity of western Canadian subsurface coal beds and methanogenic coal enrichment cultures. Int J. of Coal Geology,* 2010, 82(1-2), p 81-93) have recently characterized Alberta coal bacterial and archaeal populations to understand the microbial ecology and methanogenesis processes in coal seams. Budwill et al (WO2007/136716) have also shown the potential of adding as micronutrients, marine amino acids, to enhance microbial coalbed methane production. Marine amino acids as a marine protein hydrolysate have been shown to be preferable to other protein hydrolysates, such as soytone, tryptone, yeast extracts and brain heart infusions, in increasing coalbed methane gas output. No reason or theory is advanced for these differences in the prior art and all the methods described therein have fallen short in producing the required increase in methane production for combustion and electricity generation.

The prior art clearly shows a drop in methane production that occurs as soon as two weeks after injection of the nutrients. One solution offered in the prior art for this observation is to have continuous multiple injections of the marine protein hydrolysate into the coal deposits but this requires shutting methane recovery and power generation too frequently and does not consistently increase methane output.

Two-further limitations make it difficult to commercially use the nutrient solutions as described in the prior art for increasing biogenic methane production:

1) The amount of marine amino acids needed to increase methane production is at a minimum 60 g/MT of coal while the concentrations are very dilute at 0.006 g/L which leads to an unviable quantity of water needed per ton of treated coal.
2) The extent of additional methane gas produced by the introduction of the marine amino acids described in the prior art is not linear. Increasing the amount of nutrient concentrations actually causes the amount of methane produced to decrease and even stop thereby limiting the applicability of the prior art inventions.

One reason ascribed for this in the prior art, for example by Budwill in WO2007/136716, is the increase in build up of volatile fatty acids such as acetic and propionic acid as metabolites produced by the microorganisms, which may act as microbial growth deterrents. The only solution for this possible effect offered in the prior art is to "lower the amount of marine amino acid contacting the coal deposit as a means of reducing any inhibitory effect" but this further starves the microorganisms leading to lower methane production as well.

More recently, Barnhart & Fields (*Enhanced coal-dependent methanogenesis coupled with algal biofuels: Potential water recycle and carbon capture. Int. J. of Coal Geology*, 2017, 171, p 69-75) have shown the use of yeast extracts and algae extracts to increase biogenic methane production in coal seams. These protein nutritive solutions also suffer from the same uneconomical high cost and low increases in methane production, with no discussion of microbial growth modulating components.

There continues to be a need for new methods for increasing biogenic methane gas production from coal mines, particularly from those that have been commercially exploited and are now abandoned. Obtaining more methane gas from such depreciated and abandoned coal mines would provide a valuable commercial benefit and an additional environmental benefit.

BRIEF SUMMARY

Surprisingly, the present invention provides for a novel composition of a protein hydrolysate that contains less than 0.5 percent by weight of free tyrosine amino acid to weight of total protein hydrolysate, wherein the free tyrosine amino acid acts as an antifeedant signal for methanogenic microorganisms, hereon referred to as "PH-tyr", and a method to use the said protein hydrolysate PH-tyr to increase biogenic coal deposit methane production in a linear fashion and no decrease in methane generation over long periods of time.

The prior art describes the use of protein hydrolysates for increasing biogenic methane production from coal deposits. It further describes marine protein hydrolysates, herein referred to as "MPH" as being the most effective protein hydrolysate. However, the MPH of the prior art cannot be used to inexorably increase methane production by increasing the concentration of the MPH solution. Instead the prior art clearly describes a negative relationship with increased MPH concentration leading to a reduction and even stoppage in methane production.

The present invention has surprisingly found that this loss of linear response for methane production to increased concentrations of MPH is due to the presence of an inhibitory compound, L-tyrosine as a free amino acid, that is present in all the protein hydrolysates of the prior art. The levels of free L-tyrosine amino acid present in the protein hydrolysates correlates well with the protein hydrolysates ability to increase biogenic methane production from coal deposits. Lower levels of L-tyrosine free amino acid lead to no drop in methane production with increased concentrations of hydrolysates for increased and prolonged production of biogenic methane from said treated coal deposits.

The present invention provides a method to produce a protein hydrolysate by enzymatic hydrolysis of protein sources with peptidase enzymes that have minimal to zero exo L-tyrosine aminopeptidase or carboxypeptidase activity, such that the overall level of L-tyrosine free amino acid in the protein hydrolysate remains below the 0.5 percent antifeedant limit for any protein hydrolysate produced. The selection of such enzymes from a wide array of sources such as, bacterial, fungal, plant or animal origin is well known to one skilled in the art.

The present invention further provides a method of increasing biogenic methane production from a subterranean coal deposit, by contacting the novel PH-tyr of the present invention with a coal deposit, wherein the contacting occurs in-situ in the coal deposit and enables the unrestricted growth of the methanogenic microorganism consortia, thereby increasing and sustaining commercially exploitable production of biogenic methane gas, especially from methane-depleted coal deposits.

The present invention further provides for the novel PH-tyr of the present invention to be added to the coal deposit in an amount effective to increase the release or production of methane gas in a linearly dependent manner from any coal deposit, the amount of novel PH-tyr ranging from one gram per 0.2 $m^3$ water per 100 square meters of accessible coal surface, up to one hundred grams per 20 $m^3$ water per 100 tons of coal.

The present invention further provides that the novel PH-tyr of the present invention may optionally be used in a liquid formulation singly or mixed with other proteins, lipids, micronutrients such as vitamins and minerals and methanogenic microorganisms for direct or indirect use in coal deposits, such as in coalbeds and coal mines, to increase and sustain biogenic methane production.

DETAILED DESCRIPTION

Subterranean coal deposits are geological formations containing coal that are found below the surface of the ground. Such formations are found throughout the world and are located at varying depths and encompass coalfields, coal reservoirs, coal basins, coalbeds, coal seams, coal horizons or coal mines.

Methane gas is trapped in many subterranean coal-containing formations. The methane gas can be thermogenic or biogenic in form. Thermogenic methane gas is methane that was produced during the coal deposit formation itself and is fixed in its content in any coal deposit. Biogenic methane gas is continuously produced by a methanogenic microbiological consortia of organisms that live in the coal deposits. Biogenic methane is a renewable source of energy provided the microbiological consortium can be kept healthy and active. Commercially, the methane gas is typically obtained from the subterranean coal deposits by drilling a well into the deposit such as into a coal mine or by fracturing the coal deposit, such as with a coal bed. The released methane gas may be collected and used on site or may be transported away from the coal deposit and be used for electric power generation.

Methods are provided herein for producing novel PH-tyr and for the use of PH-tyr for increased biogenic methane gas production and release from subterranean coal deposits.

In an aspect of the invention, the novel PH-tyr is obtained from enzymatic hydrolysis of a protein source, animal, fungal, bacterial or plant. More preferably the source is from a food waste stream. Most preferably the source is a marine waste stream source.

In a further aspect of the invention, the novel PH-tyr is composed of marine waste stream peptides and amino acids that are obtained by the enzymatic hydrolysis of fish offcuts, namely the head, tail and backbone pieces that remain after fileting of the fish. The enzymatic hydrolysis process can make use of any mixture of endopeptidase and exopeptidase enzymes so long as they have minimal to zero exotyrosinase activity, many of which have been described and are known to those skilled in the art. Furthermore, descriptions of the physical processes involved in enzymatic hydrolysis and fish amino acids are also described in the art, for example, in the WO published patent application, WO2017119820, the contents and references are expressly incorporated herein by reference.

In one aspect of the present invention, the process begins with the preparation of industrial fish or fish byproducts into a size and form most suitable for rapid enzymatic hydrolysis via a process of grinding or mashing. Fish byproducts typically consists of the head, tail and backbones of fish after the fileting process. Thus, the first step of the process to make the novel PH-tyr of the present invention is directed to provide a suitable particle size and composition for carrying out the enzymatic hydrolysis.

Those skilled in the art know that enzymatic protein hydrolysis can be carried out by many known protease enzymes. These enzymes can cleave an amide bond in the middle of a protein, such enzymes being commonly known as endoproteases or cleave a protein from its N- or C-terminus, one amino acid at a time, such enzymes being commonly known as exopeptidases. Exopeptidases have selective activity for a specific amino acid or specific class of amino acids present at the N- or C-terminus. Those that do not have the ability to cleave a tyrosine amino acid from either terminus are selected from bacteria, fungi and plants, isolated and used herein. Examples of some such enzymes are shown herein. However, many more are described in the prior art, and may be used to produce the PH-tyr protein hydrolysates of the present invention and are included within the scope of this application.

In another aspect of the present invention, either endopeptidases only or a mixture of endopeptidases and non exotyrosinase peptidase enzymes are used to effect the hydrolysis of industrial fish or fish byproducts into a reaction mixture consisting of three phases (i) an aqueous phase consisting of soluble amino acids and peptides with a novel composition that contains less than two percent weight/weight of L-tyrosine either as a free amino acid or as a terminal amino acid component of any peptide, (ii) an oily lipid phase consisting of a mixture of saturated and unsaturated fatty acids and phospholipids and (iii) an insoluble solid fraction consisting of small insoluble proteins and bone fragments.

In another aspect of the present invention, the three phases after the enzymatic hydrolysis are separated using a combination of vibrating sieves with decreasing mesh size to remove the insoluble fraction followed by a centrifuge to separate the oil and aqueous fraction. The aqueous fraction may be concentrated and converted to a dry powder using any technique such as evaporation, spray drying, tray drying known in the art, to result in the novel PH-tyr powder of the present invention.

Those skilled in the art of powder formulations will recognize that individual methods for evaporation and drying may be selected in part based on the method of application for the powder being prepared and generally the methods of phase separation and drying that may be used in the process of this invention can be, without intended limitation, any such equipment or method known to one skilled in the art.

An example novel PH-tyr has a distribution of amino acids as shown in the below Table 1. Such distribution is merely demonstrative of a typical distribution and is not limiting in its scope.

TABLE 1

| Amino Acid | g/100 g |
|---|---|
| Alanine | 8.3 |
| Arginine | 7.2 |
| Aspartic acid | 9.1 |
| Cysteine | 0.4 |
| Glutamic acid | 13.7 |
| Glycine | 15.6 |
| Histidine + Glutamine | 2.0 |
| Isoleucine | 2.9 |
| Leucine | 5.6 |
| Lysine | 6.8 |
| Methionine | 2.5 |
| Phenylalanine | 3.4 |
| Proline | 7.3 |
| Serine + Asparagine | 4.9 |
| Threonine + Citrulline | 3.0 |
| Tryptophan | 0.5 |
| Tyrosine | 2.0 |
| Valine | 3.8 |

In another aspect of the present invention, novel PH-tyr are used which contain amino acids and peptides, 100% of the peptides being less than 50,000 daltons in size. In a further aspect of the invention, 90 percent or more of peptides being less than 10,000 daltons in size, and 40 percent or more of peptides being less than 3,000 daltons in size.

In another aspect of the present invention, methods are provided for increasing the release or production of methane gas from the coal deposit, the increase being shown to be relative to a prior amount of methane gas released or produced from the coal deposit, relevant to an equivalent time period and location of methane gas from the coal deposit.

In another aspect of the present invention, methods are provided for increasing the release or production of methane gas from the coal deposit by contacting it with the novel PH-tyr in a liquid formulation. The contacting may be made via a tube, well or fracture in the coal deposit using water or another liquid to disperse PH-tyr into the coal deposit. However, other methods may also be used to contact the amino acids with the subterranean coal deposit, such as dispersing the novel PH-tyr as a dust in a dry formulation.

In another aspect of the present invention, the purpose of contacting the coal deposit with the novel PH-tyr is to provide the peptides and amino acids as a nitrogen containing substrate for the microorganisms located in the coal deposit in order to increase methane production and methane release from the coal deposit. As described earlier, peptides and amino acids contacted with a subterranean coal deposit are metabolized by a consortium of microorganisms that includes the production of methane by the methanogenic microorganism consortium. In an aspect of the invention, contacting the peptides and amino acids with the coal deposit refers to locating the peptides and amino acids in the immediate proximity of the coal deposit so that a consortium of microorganisms in the formation have access to the peptides and amino acids, as nutritive substrates.

In an aspect of the invention, the novel contacting occurs in situ in the subterranean coal deposit.

In another aspect of the present invention, the subterranean coal deposit contains methanogenic microorganisms. In the context of this invention, methanogenic microorganisms are microorganisms that produce methane from naturally occurring or introduced substrates located in a subterranean coal deposit. Methane production from coal results from a series of biochemical reactions under substantially anaerobic conditions. That is, a consortium of microorganisms degrade coal in a stepwise fashion such that the products of some microorganisms serve as substrates for other microorganisms of the consortium.

In another aspect of the present invention, the novel PH-tyr of this invention contains peptides and amino acids which are degraded by hydrolytic microorganisms and fermentative anaerobic microorganisms producing monomeric compounds. The monomeric compounds produced include carbon dioxide, acetate and hydrogen gas. These monomeric compounds serve as substrates, for example, for acetogenic microorganisms which produce, for example, carbon dioxide and acetate. Methanogenic microorganisms produce methane from; for example, the carbon dioxide and acetate products of the acetogenic microorganisms.

The invention further includes contacting the subterranean coal deposit with an amount of novel PH-tyr that is effective to increase the release or production of methane gas from the coal deposit. This amount can be determined by measuring the amount of release or production of methane gas, resulting from contact with novel PH-tyr, from the coal deposit itself, for example by measuring release or production of methane gas at the location of contact or at any more remote locations in the coal deposit. This amount can also be calculated, by measuring the amount of methane produced at the location of contact or by measuring the amount of methane produced from coal deposit samples in the laboratory, that have been extracted from the coal deposit.

In an aspect of the invention, it has been discovered that the presence of free L-tyrosine amino acid above 0.5 percent weight to weight of protein hydrolysate results in a decrease of methane production from coal by methanogenic microorganisms.

In another aspect of the present invention, it has been discovered that the following amounts of novel PH-tyr per metric ton or square meter of surface area of coal can be used to increase methane production in a linearly dependent manner with no inhibitory effect observed upon increased concentration of the novel marine protein hydrolysate contacting the coal deposit: more than or equal to 1 gram but less than 100 grams; more than or equal to 100 grams but less than 1000 grams of novel marine protein hydrolysate per 100 square meter of surface or 100 metric ton of coal contacted. The volume of PH-tyr solution can range from 0.1 $m^3$ to 10 $m^3$ per 100 metric ton of coal contacted.

The invention further provides that the amount and concentrations of novel PH-tyr is determined based on the location of the coal deposit. This predetermined location may include the entire coal deposit or a portion thereof. The purpose of predetermining a location is to identify the area or areas in the coal deposit where it is desired to put the novel PH-tyr in contact with the coal deposit. For instance, depending on the attributes of the coal deposit (such as tunnels, cleats, interbeds and amount of water), the skilled artisan will make a determination of a location or locations of the coal deposit to disperse the novel PH-tyr.

Furthermore, the invention includes applying the methods herein to inactive or abandoned coal deposits and coal deposits where the methane gas has already been released from the coal deposit or methane gas is no longer being collected from the coal deposit. In addition to coal, the present invention also includes subterranean formations including the following hydrocarbon containing materials: peat, shale, tar sand, heavy oil or mixtures thereof.

As used in the context of the invention, it is to be understood that the terminology used herein is for the purpose of describing particular embodiments only, and is not intended to be limiting. It must be noted that, as used herein and in the appended claims, the singular forms "a," "an," and "the" include plural referents unless the context clearly indicates otherwise. The term "and/or" as used herein and in the appended claims, means one or both of the alternatives.

Example 1

Preparation of a novel protein hydrolysate (PH-tyr) liquid with less than 0.5 percent weight/weight of free L-tyrosine amino acid. 250 kg of head and back bone of a fish are added into a grinder and processed into 10 cm (long axis) irregular pieces. The ground material is transferred to a hydrolyzing reactor containing 250 liters of water and the stirred mixture is heated to 60 C. 25 grams of Bromelain (Enzeco), 25 grams of an Fungal Protease 400 are added into the hydrolyzing reactor and the mixture stirred for one hour. The enzymes are then rendered inactive by heating the reaction to 90 C for 5 minutes and the entire contents of the reactor are fed into a three phase decanter (tricanter) to effect the separation of three fractions, solid, lipid (oil) and aqueous. The aqueous fraction is further passed through a membrane filtering system and fed into a three phase evaporator to concentrate the dry matter concentration in the aqueous layer from approximately 8 percent before evaporation to 60 percent after evaporation, and to yield a stable viscous liquid. Analysis of the liquid shows that the concentration of free L-tyrosine amino acid is 0.25 percent weight to weight of dry matter in the liquid.

Example 2

Preparation of a marine protein hydrolysate (MPH) liquid of the prior art. 250 kg of head and back bone of salmon are added into a grinder and processed into 10 cm (long axis) irregular pieces. The ground material is transferred to a hydrolyzing reactor containing 250 liters of water and the stirred mixture is heated to 60 C. 50 grams of commercially available Protamex™ is added into the hydrolyzing reactor and the mixture stirred for one hour. The enzyme is then rendered inactive by heating the reaction to 90 C for 10 minutes and the entire contents of the reactor are fed into a three phase decanter to effect the separation of three fractions, solid, lipid (oil) and aqueous. The aqueous fraction is further passed through a membrane filtering system and fed into a three phase evaporator to concentrate the dry matter concentration in the aqueous layer from less than 8 percent before evaporation to 35 percent after evaporation, and to yield a stable viscous liquid. Analysis of the liquid shows that the concentration of free L-tyrosine amino acid is 0.95 percent weight to weight of dry matter in the liquid.

Example 3

Alternate preparation of a marine protein hydrolysate (MPH) liquid of the prior art. 250 kg of head and back bone of salmon are added into a grinder and processed into 10 cm (long axis) irregular pieces. The ground material is transferred to a hydrolyzing reactor containing 250 liters of water and the stirred mixture is heated to 60 C. 25 grams of Alcalase™ 2.4 L and 25 grams of Novozym™ FM 2.0 L are added into the hydrolyzing reactor and the mixture stirred for one hour. The enzyme is then rendered inactive by heating the reaction to 90 C for 10 minutes and the entire contents of the reactor are fed into a three phase decanter to effect the separation of three fractions, solid, lipid (oil) and aqueous. The aqueous fraction is further-passed through a membrane filtering system and fed into a three phase evaporator to concentrate the dry matter concentration in the aqueous layer from 12 percent before evaporation to 35 percent after evaporation, and to yield a stable viscous liquid. Analysis of the liquid shows that the concentration of free L-tyrosine amino acid is 0.7 percent weight to weight of dry matter in the liquid.

Example 4

Preparation of a novel marine protein hydrolysate (PH-tyr) powder with less than 0.5 percent weight/weight of free L-tyrosine amino acid. 250 kg of head and back bone of salmon are added into a grinder and processed into 10 cm (long axis) irregular pieces. The ground material is transferred to a hydrolyzing reactor containing 250 liters of water and the stirred mixture is heated to 60 C. 50 grams of papain are added into the hydrolyzing reactor and the mixture stirred for one hour. The enzyme is inactivated by lowering the pH of the reaction to 4.0 using hydrochloric acid and the entire contents of the reactor are fed into a three phase decanter to effect the separation of three fractions, solid, lipid (oil) and aqueous. The aqueous fraction is further passed through a membrane filtering system that concentrates the dry matter in the liquid to 30-35% percent. The output liquid is spray dried at 140 degree C. to give a dry powder with 94-99 percent dry matter. Analysis of the powder shows that the concentration of free L-tyrosine amino acid is 0.25 percent weight to weight of total powder.

Example 5

Alternate preparation of a novel marine protein hydrolysate (PH-tyr) powder with less than 0.5 percent weight/weight of free L-tyrosine amino acid. 250 kg of head and back bone of salmon are added into a grinder and processed into 20 cm (long axis) irregular pieces. The ground material is transferred to a hydrolyzing reactor containing 250 liters of water and the stirred mixture is heated to 55 C. 25 grams of commercially available papain and 25 grams of commercially available 1:1 mixture of leucine aminopeptidase and glycine carboxypeptidase enzymes are added into the hydrolyzing reactor and the mixture stirred for 1 hour. The exopeptidase enzymes are acidic enzymes derived from *Bacillus subtilis*. The enzymes are then rendered inactive by heating the reaction to 90 C for 10 minutes and the entire contents of the reactor are fed into a vibrating sieve containing mesh separators of various sizes to effect the separation of the solid and liquid fractions. The liquid fraction is further separated into the lipid (oil) and aqueous fractions using a centrifuge. The aqueous fraction is then passed through a microfiltration unit followed by a nanofiltration system, such as those described in the prior art, that removed particles above 100 micron in size and simultaneously concentrated the dry matter in the aqueous liquid, to yield a stable novel PH-tyr liquid with approximately 30 percent dry matter. The output from the nanofiltration is spray dried at 140 degree C. to give a dry powder (PH-tyr powder) with 95 percent dry matter. Analysis of the powder showed that the concentration of free L-tyrosine amino acid is 0.2 percent weight to weight of total powder.

Example 6

Methane Generation Comparison Examples. Comparison of the effect between MPH of the prior art and the novel PH-tyr to enhance and/or increase biogenic methane production from coal. Increased methane gas production examples with crushed and core coal were conducted at close to atmospheric pressures in sealed glass reactors. Variance on the presence or absence of L-tyrosine in the marine protein hydrolysate and the relationship with methanogenesis rates while varying the amount and concentration of the hydrolysates is reported herein.

Three different methanogenic cultures enriched from coal bed methane producing coal deposits were used herein as shown in Table 2. The cultures were incubated, without shaking, at different temperatures ranging from 30 to 50° C., in the dark.

TABLE 2

Methanogenic cultures used for comparison

| Culture Name | Method |
| --- | --- |
| FRP030 | Enriched from a methane producing coal mine sample and grown at 30° C. |
| FRP050 | Enriched from a methane producing coal mine sample and grown at 35° C. |
| USSPH010 | Enriched from a coal core taken from a coalbed methane well, grown at 30° C. |

All three cultures showed similar methanogenic activity and were used interchangeably in the examples below. The growth medium for culturing the coal samples additionally consisted of mineral salts, such as described in the prior art, that had been boiled for 2-3 minutes and deoxygenated by bubbling nitrogen for 10 minutes through the liquid and stored oxygen free in rubber stopper inoculation flasks. Both the MPH of the prior art and the novel PH-tyr of the present invention were used in either liquid (30% dry matter) or in powder (95% dry matter) form with no difference observed between the liquid and powder formulations. All samples were kept frozen at −20 C until used for the experiments.

In order to demonstrate that the free L-tyrosine amino acid in MPH was inhibiting methanogenesis, several experiments were set up at various concentrations to compare MPH and PH-tyr. As can be seen in FIG. 1,using 0.5 grams of coal and USSPH010 culture, methane production for MPH decreased as concentration was increased beyond at 0.005 g/ml, whereas methane production with PH-tyr continued to rise well beyond the 0.005 g/ml threshold. PH-tyr showed proportional increased methane production up to 0.05 g/ml concentration which is 10× more than the highest level of 0.005 g/ml for MPH.

Further increase in concentration to 0.5 g/ml for PH-tyr also gave higher methane production although not a proportional increase, perhaps lending further proof for the negative effects of free L-tyrosine amino acid which is still present at approximately 0.2-0.25 percent weight to weight in the PH-tyr tested herein.

Further as can also be seen in FIG. 1, no plateau or decrease in methane production was observed for the PH-tyr between 5 to 15 days nor after 40 to 45 days, as was observed for the optimum MPH treatment at 0.005 g/ml.

FIG. 1—Comparison of MPH and PH-tyr in methane production

FIG. 1 shows that treatment with the PH-tyr peptide mix, which contains a relatively much lower concentration of tyrosine, results in higher, time sustained methane production and with a good dose response as compared to the MPH peptide mix which contains more tyrosine.

The prior art also describes a method to increase methanogenesis with MPH by diluting the concentration of the MPH and applying the diluted MPH solution more periodically. The prior art describes that this may reduce the amount of VFA such as acetic acid which may be growth inhibitory in nature and be the cause of the lower methanogenesis. The prior art further claims that the use of a more dilute solution is cheaper, even though the total amount of nutrient applied by periodic application is almost the same. More importantly, the prior art does not take into consideration the very significant cost of water and the cost of spraying much larger volumes into coal deposits as well as the significant environmental burden placed by the use of much larger volumes of water.

Example 7

Figure 2:
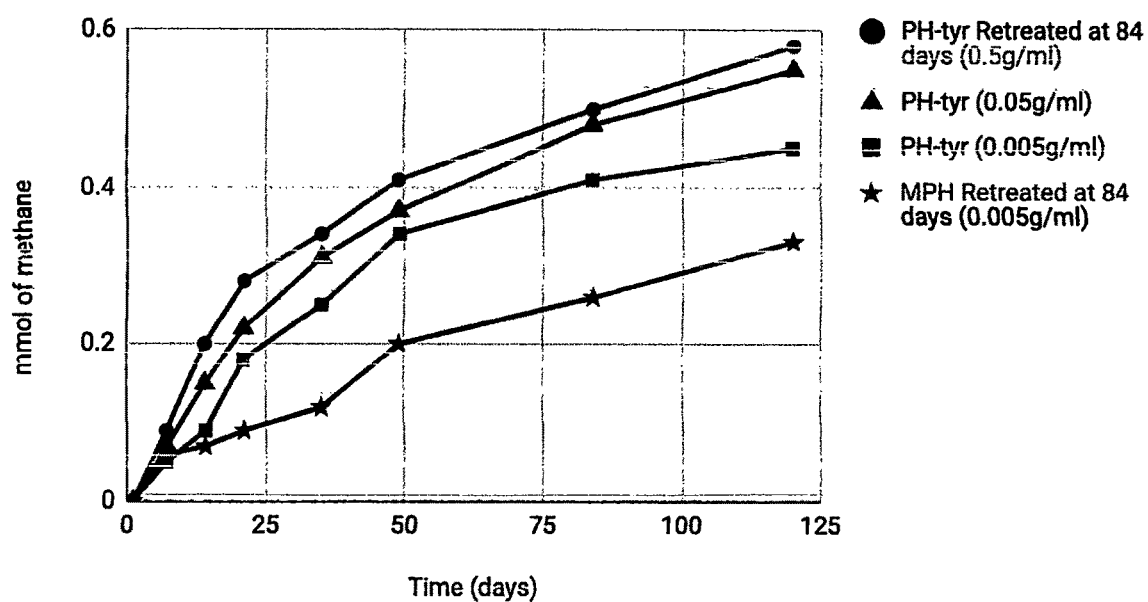

In this example, we show that PH-tyr is effective at much higher concentrations than MPH (10×-100×) bringing the volume, cost and environmental impact of water use to a minimum as compared to the prior art. The addition of MPH at 0.005 g/ml and PH-tyr at 0.005 g/ml to 0.5 g/ml concentrations provided an increased production of methane from methanogenesis in the presence of coal. In the case of MPH at 0.005 g/ml and PH-tyr at 0.5 g/ml concentrations the methane production rates in the cultures began to reduce approximately 80 days post treatment. Example 6 investigated the effect of dosing the MPH and PH-tyr treated cultures at 84 days post treatment with additional amounts of the MPH and PH-tyr at the same concentrations. As can be seen in FIG. 2, modest increases in methane production is observed upon redosing but the increase is not proportional to the additional quantities of nutrients added for both treatments due to the higher presence of free L-tyrosine amino acid.

FIG. 2—Retreatment at 84 days of MPH (0.005 g/ml) and PH-tyr (0.5 g/ml)

FIG. 2 shows the abiliy of PH-tyr to generate a 2 fold increase in methane production at 100x the concentration of MPH while showing only a modest increase at a midpoint retreatment, together showing a reduction in the potential cost of methane generation.

Example 8

Figure 3:
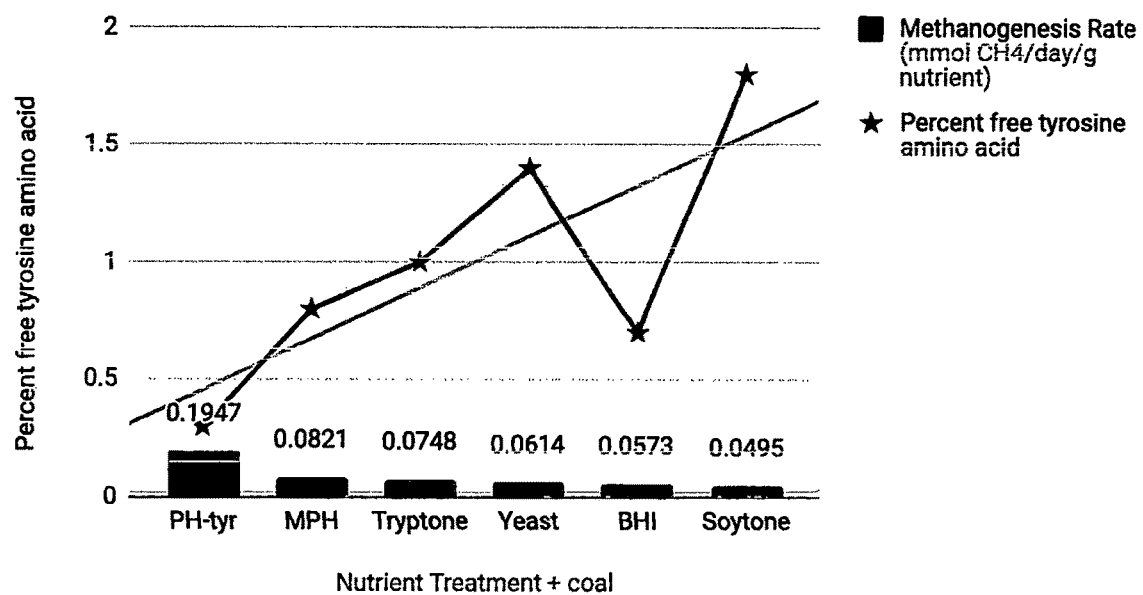

To further validate the negative effect of free L-tyrosine amino acid on methanogenesis in coal deposits, we compared the methanogenesis rates of other nutrient solutions Brain-Heart Infusion (dehydrated infusion of beef or porcine brains and hearts), yeast extract (water soluble portion of autolyzed yeast containing a vitamin B complex), soytone (enzymatic digests of plant proteins), and tryptone (enzymatic digest of casein, the main protein of milk) and PH-tyr at 0.005 g/ml concentration and plotted this against the concentrations of free L-tyrosine amino acid in each of them as shown in FIG. 3 below. Although a perfect correlation is absent due to the results from the Brain Heart Infusion nutrient, the trend (as shown in the trendline in FIG. 3) for increased free L-tyrosine amino acid leading to decreased biogenic methane production can be noted. The BHI result may have a simple explanation, since it is the only whole protein extract tested with larger protein molecules leading to reduced methanogenesis versus the other nutrients which are all hydrolyzed extracts, containing much smaller peptides and more free amino acids.

FIG. 3—Comparing Methanogenesis Rate (mmol CH4/day/g nutrient) versus Percent of Free Tyrosine amino acid present in nutrient FIG. 3 shows the inverse linear relationship between the percent of tyrosine present in a nutrient and the rate of methane generation. The linear least fit line shown in the image shows that as the amount of tyrosine in the different nutrients increases, the rate of methane generation decreases.

The examples demonstrate how the addition of PH-tyr greatly enhanced methane production by acting as a source of nitrogen for the methanogenic microorganism consortium which seem to be lacking a nutrient nitrogen source.

Example 9

Figure 4:
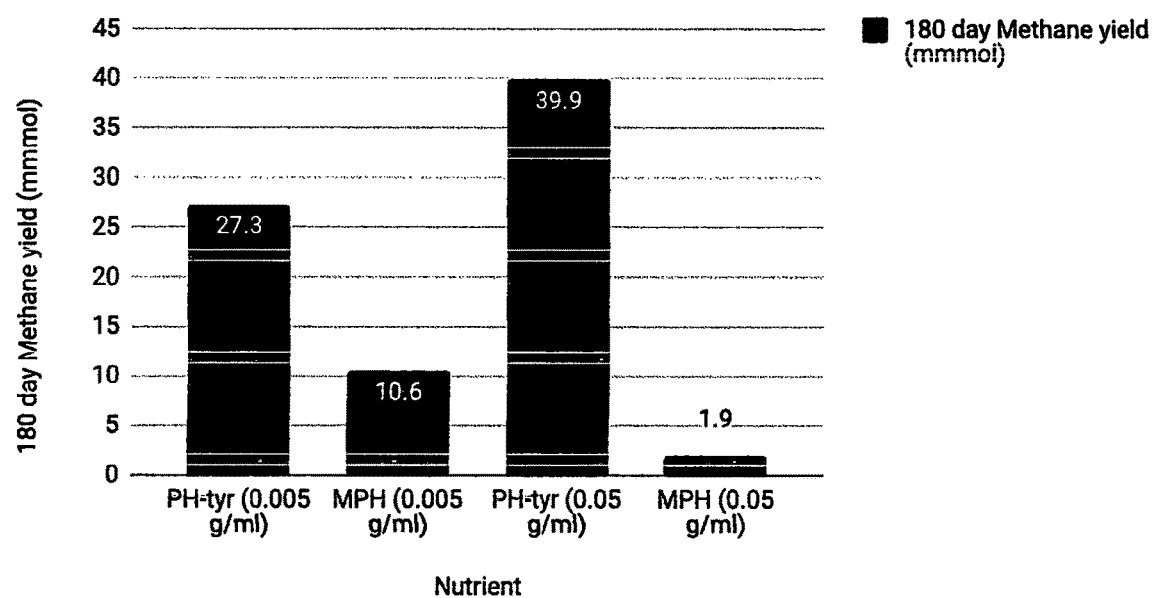

In this example, PH-tyr was used under high pressure conditions to simulate methane recovered from coal beds using fracking methodology. Into four identical 300 ml stainless steel vessels (A; B; C; D) with a maximum pressure rating of 500 psi was added 10 g crushed coal, 100 ml of mineral salt mixture, FRP050 inoculum each. Into vessel A was added 0.005 g/ml of PH-tyr, into Vessel B was added 0.005 g/ml of MPH, into Vessel C was added 0.05 g/ml of PH-tyr and into Vessel D was added 0.05 g/ml of MPH. The vessels were initially pressurized to 24 psi with 100% oxygen-free nitrogen. After a week of incubation at 30 C, the pressure was increased to 50 psi and after another week of incubation, to a final pressure of 150 psi. The vessels were held at 150 psi and 30 C for 182 days. This period signified the entire growth period of the experiment. A pressure transducer on the vessel recorded pressure changes within the vessels in real time. Increased methane production was directly assayed using a gas sampler syringe on a HP microGC with argon carrier gas, Inlet temp 100 C, column temp 60 C, Outlet temp 100 C on a SP-30 stationary phase fused silica column (5 m). FIG. 4 shows the results of the experiment with PH-tyr being much more methanogenic at both concentrations as compared to MPH.

FIG. 4—150 psi, 180 day Methane yield (mmol) for PH-tyr and MPH Nutrients

FIG. 4 describes the results of a simulated field test using actual coal mine core samples. The lower levels of tyrosine present in PH-tyr versus MPH nutrients shows a greater than 20 fold increase in methane production over 180 days at 0.05 mg/ml concentration.

Example 9 demonstrates that the addition of PH-tyr greatly stimulated methanogenic microbial activity and stimulated the cultures to grow and produce methane at elevated pressures as would be encountered in the deep subsurface coalbeds and coal deposits.

What is claimed is:

1. A method comprising contacting methanogenic microorganisms in a subsurface coal formation with a composition of amino acids wherein the amino acid L-tyrosine is less than 0.5 percent by weight to weight of the total amino acids present in the composition, and wherein the composition of amino acids is produced by a enzymatic hydrolysis of protein using enzymes selected from the group consisting of bromelain, papain, leucine aminopeptidase and glycine carboxypeptidase.

2. The method according to claim 1 wherein the composition may be in a liquid aerosolized form.

3. The method according to claim 2 wherein the composition may additionally contain other nutrients.

4. A method of increasing methane gas production from a subsurface coal formation by contacting said coal formation with a composition of amino acids wherein the amino acid L-tyrosine is less than 0.5 percent by weight to weight of the total amino acids present in the composition, and wherein the composition of amino acids is produced by enzymatic hydrolysis of protein using enzymes selected from the group consisting of bromelain, papain, leucine aminopeptidase and glycine carboxypeptidase.

* * * * *